(12) United States Patent
Hacker et al.

(10) Patent No.: US 8,427,653 B2
(45) Date of Patent: Apr. 23, 2013

(54) OPTICAL COHERENCE TOMOGRAPHY METHODS AND SYSTEMS

(75) Inventors: Martin Hacker, Jena (DE); Christoph Hauger, Aalen (DE); Keith O'Hara, Livermore, CA (US); Scott Meyer, Livermore, CA (US)

(73) Assignees: Carl Zeiss Meditec AG, Jena (DE); Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 13/007,470

(22) Filed: Jan. 14, 2011

(65) Prior Publication Data

US 2011/0176142 A1    Jul. 21, 2011

Related U.S. Application Data

(63) Continuation of application No. PCT/EP2009/005152, filed on Jul. 15, 2009.

(60) Provisional application No. 61/081,343, filed on Jul. 16, 2008.

(51) Int. Cl.
*G01B 11/02* (2006.01)

(52) U.S. Cl.
USPC .......................................................... 356/497

(58) Field of Classification Search .................. 356/456, 356/479, 497
See application file for complete search history.

(56) References Cited

U.S. PATENT DOCUMENTS

| | | | |
|---|---|---|---|
| 5,956,355 | A | 9/1999 | Swanson et al. |
| 7,330,270 | B2 | 2/2008 | O'Hara et al. |
| 7,336,366 | B2 | 2/2008 | Choma et al. |
| 7,570,364 | B2 * | 8/2009 | Kuroiwa ...................... 356/479 |
| 7,602,500 | B2 * | 10/2009 | Izatt et al. ..................... 356/497 |

(Continued)

FOREIGN PATENT DOCUMENTS

| | | |
|---|---|---|
| DE | 10 2005 046 690 A1 | 5/2006 |
| JP | 2006-101927 A | 4/2006 |
| WO | WO 2006/077106 A1 | 7/2006 |

OTHER PUBLICATIONS

Fercher et al., "Optical coherence tomography—principles and applications" Reg. Prog. Phys. 2003; 66(2):239-303.

(Continued)

*Primary Examiner* — Tarifur Chowdhury
*Assistant Examiner* — Johnathan Hansen
(74) *Attorney, Agent, or Firm* — Potomac Patent Group PLLC

(57) ABSTRACT

Frequency domain optical coherence tomography (FD-OCT) systems and methods are provided. Thereby, a first measurement and a second measurement is performed, wherein in the first measurement an object region is illuminated by measuring light having a spectrum with a first spectral width and in the second measurement the object region is illuminated with measuring light having a spectrum with a second spectral width, wherein the first spectral width is at least 10% greater than the second spectral width. Further, during the first measurement intensities of spectral ranges of light having interacted with the object and being superimposed with reference light are detected, wherein a width of these spectral ranges is greater than a corresponding width during the second measurement. Thus, switching an axial field of view of structural information of the object across a depth direction is enabled upon minimizing radiation damage at the object.

43 Claims, 5 Drawing Sheets

U.S. PATENT DOCUMENTS

| | | |
|---|---|---|
| 7,692,797 B2 * | 4/2010 | Kawahara .................... 356/497 |
| 2006/0066869 A1 | 3/2006 | Ueno et al. |
| 2006/0164639 A1 | 7/2006 | Horn et al. |
| 2007/0002327 A1 * | 1/2007 | Zhou et al. .................... 356/456 |
| 2007/0024856 A1 * | 2/2007 | Izatt et al. .................... 356/479 |
| 2007/0076220 A1 * | 4/2007 | Kawahara .................... 356/497 |
| 2007/0291277 A1 | 12/2007 | Everett et al. |
| 2008/0117424 A1 * | 5/2008 | Teramura et al. ............. 356/450 |
| 2008/0151260 A1 | 6/2008 | Kikawa et al. |

OTHER PUBLICATIONS

Huber et al., "Amplified, frequency swept lasers for frequency domain reflectometry and OCT-imaging: design and scaling principles" Opt Express. May 2, 2005;13(9):3513-28.

International Search Report and Written Opinion of PCT Application No. PCT/EP2009/005152, mailed Nov. 5, 2009, 10 pages total.

* cited by examiner

OPTICAL COHERENCE TOMOGRAPHY METHODS AND SYSTEMS

CROSS-REFERENCES TO RELATED APPLICATIONS

The present application claims priority to and is a continuation of International Patent Application No. PCT/EP2009/005152, filed on Jul. 15, 2009 and claims benefit under 35 U.S.C. §119(e) of U.S. Provisional Patent Application No. 61/081,343, filed on Jul. 16, 2008, the disclosures of which are hereby incorporated by reference in their entirety for all purposes.

BACKGROUND OF THE INVENTION

The present invention relates to optical coherence tomography (OCT) systems and methods. In particular, the present invention relates to frequency domain optical coherence tomography (FD-OCT) systems and methods. In particular, the present invention relates to FD-OCT systems and methods capable of adjusting an axial field of view of structural data acquired from an object.

Optical coherence tomography (OCT) is an optical interferometric method for gaining structural information about an object. For this, the object is illuminated with measuring light having a particular spectrum indicating an intensity distribution of the measuring light in dependence of wavelengths comprised in the measuring light. Such a spectrum may be characterized by at least two parameters, a mean wavelength (or peak wavelength) and a spectral width of the spectrum. The mean wavelength may be obtained as a 0th moment of the spectrum. The spectral width of the spectrum may be considered as a spectral range around the mean wavelength, wherein an accumulated intensity of light having wavelengths within this wavelength range amounts to a major portion of a total intensity of the measuring light.

A coherence length of the measuring light is proportional to a ratio between the square of the mean wavelength and the spectral width. The coherence length of the measuring light determines under which conditions interference between two different light portions of the measuring light may be observed. Interference of two light portions of the measuring light can only be observed, if a difference of optical paths traveled by the two light portions differs by less than the coherence length. This property is exploited in different implementations of optical coherence tomography.

In different implementations of OCT the object is illuminated by at least a first portion of the measuring light having a low coherence length. Depending on the material comprised in the investigated object, the mean wavelength of the spectrum of the measuring light, and other physical properties, the intensity of the measuring light penetrating the object exponentially decreases characterized by a particular penetration depth. The penetration depth may amount for example to 1 mm to 3 mm for biological objects such as tissue, if the mean wavelength is in a range of for example 800 nm to 1300 nm. Measuring light penetrated into the object up to a particular depth within the object interacts with the material present within a volume of the object at that depth which comprises scattering and reflection processes. In particular, a reflectivity within a volume of the object depends on a refractive index and a gradient of the refractive index of the material within the particular volume of the object. Also, an orientation of an interface between two volume portions within the object having different refractive indices relative to a direction of a beam path of the measuring light influences the amount of reflected light emanating from the object in a particular direction. In OCT, typically measuring light returning from the object in a direction opposite to the direction of the incident measuring light is detected.

A second portion of the measuring light traverses an optical beam path which optical path length is controlled by a position of e.g. a reflecting surface. The first portion of the measuring light having interacted with the object at a certain depth and the second portion of the measuring light beam being reflected at the reflecting surface arranged at a certain position are superimposed and detected.

The different implementations of OCT differ in the way the object is probed at different depths and also in the way the detecting the superimposed measuring light is performed.

In time domain OCT (TD-OCT) probing different depths of the object (that is performing an axial scan) is performed by displacing the reflecting surface at which the second portion of the measuring light is reflected before superimposing the second portion with the first portion of the measuring light having interacted with the object. As explained above, only that part of the first portion of the measuring light that interacted with material in the object at a depth having traversed an optical path length whose difference to an optical path length traversed by the second portion of the measuring light is smaller than the coherence length of the measuring light will contribute to the detected intensity of the superimposed light. Thus, by displacing the reflecting surface structural data from different depths within the object may be acquired.

In frequency domain OCT (FD-OCT) the second portion of the measuring light is also reflected at a reflecting surface but this reflecting surface need not to be displaced in order to probe different depths of the object that means to perform an axial scan. Instead, structural information about the object in different depths, i.e. in particular reflectivities in different depths, are obtained by detecting intensities of the superimposed light in dependence of a wavelength of the superimposed light. For this, mainly two techniques or variations of OCT have been developed, namely spectral domain OCT (SD-OCT) and swept-source OCT (SS-OCT).

In spectral domain OCT the superimposed light comprised of a first portion of measuring light having interacted with the object and a second portion of the measuring light being reflected at a reflecting surface is spectrally dispersed using a spectrometer which e.g. detects the spectrally dispersed and thus spatially separated superimposed light by a positionally resolving detector. The positionally resolving detector typically comprises plural detector segments, wherein each segment receives a spectral portion of the superimposed light. Thereby, the positionally resolving detector supplies a spectrum of the superimposed light for further processing. By Fourier transformation of the spectrum of the superimposed light a distribution of reflectivities of the object along an axial direction, i.e. a depth direction, is obtained.

An axial field of view or depth field of view (FOV) of the SD-OCT method depends on a width of a spectral range of a spectral portion received by one of the segments of the positionally resolving detectors, i.e. the spectral resolution. The smaller the width of the spectral range of the spectral portion of the superimposed light received by a segment of the detector, the larger the axial field of view. In contrast thereto, an axial resolution or depth resolution of the obtained distribution of reflectivities within the object, i.e. the structural information, depends on a total spectral range of the superimposed measuring light detected by the plural segments of the positionally resolving detector.

In swept-source OCT (SS-OCT) a sweepable light source generating measuring light having a spectrum with a spectral width much narrower than a spectral width of a spectrum of measuring light used in spectral domain OCT is used to illuminate the object. A first portion of such measuring light returned from the sample and superimposed with a second portion of the measuring light is detected by a photo-detector without the need of previously spectrally dispersing the superimposed light. A spectrum of the superimposed measuring light at different wavelengths of the measuring light is obtained by sweeping a mean wavelength of the measuring light over time and concurrently detecting the superimposed light. An envelope of a spectrum of the measuring light cumulated over time during such sweeping may correspond to a typical spectrum of measuring light used in SD-OCT.

In SS-OCT the axial field of view (FOV) depends on a spectral width of the measuring light at every point in time, i.e. the maximum spectral resolution, e.g. achieved by time resolved detection.

From document US 2007/0024856 A1 an optical coherence imaging system is known, wherein an effective line width of the detected superimposed light can be reduced using periodic optical filters thereby increasing the axial field of view. However, accurate adjustments of the periodic optical filters are required.

Document DE 10 2005 046 690 A1 discloses a spectral domain OCT system, wherein a lens group having an adjustable focus length is arranged between a diffraction grating and a positionally resolving detector. Thereby, an axial field of view of the object can be varied by adjusting the focal length of the lens group and displacing the detector relative to the lens group.

However, the conventional OCT systems either require expensive components, elaborate adjustments of components, or exhibit disadvantages regarding sensitivity or a required total intensity of measuring light illuminating the object.

It is therefore an object of the present invention to improve conventional OCT systems and methods to enable effective measurement of sensitive objects.

SUMMARY OF THE INVENTION

The present invention has been accomplished taking the above problems into consideration.

According to an embodiment of the present invention, a spectral domain optical coherence tomography (SD-OCT) method is provided which comprises performing a first measurement and a second measurement, wherein each measurement comprises illuminating an object region with measuring light, superimposing measuring light returned from the object region with reference light, spectrally dispersing the superimposed light, and detecting intensities of plural spectral portions of the spectrally dispersed light. Thereby, during the first measurement, the measuring light illuminating the object region is spectrally distributed according to a first spectrum and during the second measurement the measuring light illuminating the object region is spectrally distributed according to a second spectrum, wherein a first spectral width of the first spectrum is at least 10% greater than a second spectral width of the second spectrum.

A spectrum of the measuring light illuminating the object region may thereby be affected by several factors such as by a spectrum of a light source generating light, a medium of an illumination beam path traveled by the light generated by the light source, or by a spectral characteristics of a spectral filter, such as a transmission spectral filter or a reflective spectral filter arranged in an illumination beam path. The spectrally dispersing the superimposed light may comprise refracting, diffracting or filtering the superimposed light. Thus, the spectrally dispersing the superimposed light may result in spatially or temporarily separating the superimposed light. Detecting spatially separated plural different spectral portions may comprise concurrently detecting the spectral portions. Detecting temporarily separated plural different spectral portions may comprise temporarily subsequently detecting the spectral portions.

In the first measurement the object region is illuminated with measuring light having a first spectrum with a first spectral width and in the second measurement the object region is illuminated with measuring light having a second spectrum with a second spectral width. The first spectral width is at least 10% greater than the second spectral width. A spectral width of a spectrum of light characterizes a width of a wavelength range within which most of the intensity of the measuring light having the spectrum lies. A spectral width of a spectrum of the measuring light is inversely proportional to a coherence length of the measuring light. Thus, in the first measurement the measuring light has a coherence length that is at least about 10% smaller than a coherence length of the measuring light in the second measurement.

According to an embodiment of the present invention, the first spectral width is determined to be a minimum of a difference between a first upper wavelength and a first lower wavelength, wherein during the first measurement an intensity of the first measuring light having wavelengths between the first lower wavelength and the first upper wavelength amounts to 90% of a total intensity of the measuring light, and wherein the second spectral width is determined to be a minimum of a difference between a second upper wavelength and a second lower wavelength, wherein during the second measurement an intensity of the measuring light having wavelengths between the second lower wavelength and the second upper wavelength amounts to 90% of a total intensity of the measuring light.

According to an embodiment of the present invention, in the first measurement the plural different spectral portions are within a predetermined first detection wavelength range and in the second measurement the plural different spectral portions are within a predetermined second detection wavelength range, wherein a width of the first detection wavelength range is at least 10% greater than a width of the second detection wavelength range. By illuminating the object region with measuring light having different spectral widths, superimposing measuring light returned from the object region with reference light, and detecting the plural different spectral portions of spectrally dispersed superimposed light different axial resolutions of measured structural information within the object are achievable. A total intensity of measuring light illuminating the object region may be larger in the first measurement than in the second measurement or may be substantially equal.

Each of the plural different spectral portions of the spectrally dispersed light comprises light having wavelengths within a particular wavelength range. The first detection wavelength range is given by a unification of such wavelength ranges of the plural different spectral portions and the second detection wavelength range is analogously given by a unification of such wavelength ranges of the plural different spectral portions in the second measurement. Thus, according to this embodiment of the present invention, not only the first spectral width of the measuring light illuminating the object region during the first measurement is greater than the second spectral width of the measuring light illuminating the object region during the second measurement, but also a range of wavelengths comprised in the superimposed measuring light detected during the first measurement is greater than a range of wavelengths comprised in the superimposed measuring light detected during the second measurement.

According to an embodiment of the present invention, a ratio between the width of the first detection wavelength range and the first spectral width amounts to at least 0.7, in particular to at least 0.9. Thus, light constituting a major portion of the first spectrum of the measuring light illuminating the object region is, after being returned from the object region, superimposed with reference light, spectrally dispersed, and finally detected.

According to an embodiment of the present invention, a ratio between the width of the second detection wavelength range and the second spectral width amounts to at least 0.7, in particular to at least 0.9. Thereby, also during the second measurement the detecting is arranged to detect light constituting a major portion of a wavelength range comprised in the second spectrum of the measuring light illuminating of the object region.

According to an embodiment of the present invention, a width of a wavelength range comprised in each of the spectral portions during the first measurement is greater than a width of a wavelength range comprised in each of the spectral portions during the second measurement. During the first measurement the spectral portions are separately detected and during the second measurement the spectral portions are separately detected. A width of a wavelength range comprised in a detected spectral portion during the first measurement affects a field of view (FOV) during the first measurement. If a width of a wavelength range comprised in a spectral portion during the first measurement is greater than a corresponding width during the second measurement, an axial field of view during the first measurement is smaller than an axial field of view during the second measurement. In particular, these axial fields of view may differ by at least 10%, in particular by at least 20%, further in particular by at least 50%. For example, the axial field of view may be 5 to 8 mm, in particular 6 mm, during the first measurement and 1 to 3 mm, in particular 2 mm, during the second measurement. A mean wavelength of the measuring light during the first and second measurements may be within 800 nm to 1300 nm, and the first spectral width in the first measurement may be 15 to 30 nm, in particular 25 nm.

According to an embodiment of the present invention, the detecting the intensities of the plural different spectral portions comprises detecting the intensities at plural different positions of a positionally resolving detector. Thereby, the different spectral portions are spatially separated by the spectrally dispersing the superimposed light. The positionally resolving detector may be for example a CCD camera or CMOS-sensor.

According to an embodiment of the present invention, in at least one of the first and second measurements the dispersing the superimposed light comprises diffracting the superimposed light at a first diffraction grating. The first diffraction grating may comprise a substrate and plural grating forming structures arranged thereon. The grating forming structures may influence an amplitude and/or a phase of the superimposed light being incident onto the diffraction grating. The grating forming structures may be periodically arranged on the substrate of the diffraction grating. Light portions of the superimposed light comprising different wavelengths are deflected upon incidence onto the diffraction grating at angles dependent on the wavelengths comprised in the light portions. The deflection angle not only depends on the wavelength of the light portions but also on a spacing of the grating forming structures. Typically, the grating forming structures are periodically arranged having a distance, also called a lattice constant, between corresponding portions of neighbouring grating forming structures. The grating forming structure may be periodic in at least one lateral direction of the diffraction grating.

According to an embodiment of the present invention, the dispersing the superimposed light comprises allowing the diffracted light traversing an imaging optics. The imaging optics thereby may comprise one or several refractive and/or reflective elements such as lenses and/or mirrors. A focal length of the imaging optics may be adjustable, in particular by displacing at least one element of the imaging optics relative to other elements of the imaging optics.

According to an embodiment of the present invention, during both the first and the second measurements the dispersing the superimposed light comprises diffracting the superimposed light at the first diffraction grating, wherein during the first measurement the imaging optics has a first focal length and during the second measurement the imaging optics has a second focal length that is least 10% greater than the first focal length. By providing such an imaging optics having a first focal length and a second focal length the spectrally dispersed superimposed light may be imaged to a substantially same area during the first measurement and the second measurement. This advantageously enables using a single positionally resolving detector during both the first and the second measurements.

According to an embodiment of the present invention, during the second measurement the dispersing the superimposed light comprises diffracting the superimposed light at a second diffraction grating, wherein a lattice period of the first diffraction grating is at least 10% greater than a lattice period of the second diffraction grating. The greater a lattice period or lattice constant of the first diffraction grating, the smaller is an angle of light having a particular wavelength deflected by diffracting the light using the first diffraction grating. Thus, using the first diffraction grating during the first measurement and using the second diffraction grating during the second measurement to diffract the superimposed light enables to disperse the superimposed light during the first measurement and the second measurement to be spatially separated and to be detected at a substantially same area of a single positionally resolving detector.

According to an embodiment of the present invention, the respective illuminating the object region comprises scanning an illumination beam of measuring light across the object region, the illumination beam having a beam waist located at an average depth of the object region such that a Rayleigh range of the illumination beam substantially corresponds to an axial field of view of the OCT method. A beam waist is a minimal lateral extension of a measuring light beam bundle, which is preferably located at the object region. The lateral extension of the measuring light beam bundle will increase to the square root of 2 times the waist a distance of half the Rayleigh range away from the location of the waist along a direction of propagation of the measuring light. Via the scanning it is possible to acquire not only structural data across a depth direction at a single lateral point of the object region, but to acquire structural data along a depth direction of the object at plural different lateral positions of the object to acquire structural data of a volume portion defined by a lateral scanning range and an axial field of view during the first measurement and an axial field of view during the second measurement, respectively. Further, by this provision the lateral resolution of the acquired structural data does not significantly change across the depth direction.

According to an embodiment of the present invention, the method further comprises changing a difference between an optical path traversed by the measuring light and an optical path traversed by the reference light.

According to an embodiment of the present invention, a spectral domain optical coherence tomography (SD-OCT) system is provided, wherein the system comprises an illumination system having a light source for illuminating an object region with measuring light, wherein a spectral width of a spectrum of the measuring light is adjustable; a spectrometer having an adjustable dispersion for spectrally dispersing measuring light returned from the object region and superimposed with reference light into plural spatially separated different spectral portions; and a controller for adjusting the adjustable spectral width and adjusting the adjustable dispersion of the spectrometer based on an input signal.

The light source may be for example a super-luminescent diode, generating measuring light having a spectrum with a mean wavelength of 800 nm to 1300 nm and a spectral width of 5 nm to 100 nm, preferably 15 nm to 30 nm, the latter corresponding to axial resolutions of 10 m to 50 m in air. The spectral width of the spectrum of the measuring light may be adjusted by either adjusting a spectrum of the light generated by the light source, e.g. the super-luminescent diode, or by arranging a suitable spectral filter into an illumination beam path. For example, a spectral width of a spectrum generated by a super-luminescent diode may be adjusted by adjusting an electric current supplied to the super-luminescent diode.

The spectrometer may comprise refractive and/or diffractive optical elements such as a diffraction grating, a lens, or/and a prism. The spectrometer having the adjustable dispersion allows either spatially or temporarily separating spectral portions of the superimposed light according to an adjustable amount. For example, a spatial distance between two spatially separated spectral portions of light may be adjustable. This may be for example achieved by diffracting the superimposed light at different diffraction gratings having different lattice constants.

The controller is adapted to adjust the adjustable spectral width and to adjust the adjustable dispersion of the spectrometer based on an input signal. The input signal may be directly or indirectly supplied by a user or any other component of the system. The adjusting the adjustable spectral width and the adjustable dispersion of the spectrometer may occur in mutual dependency, i.e. the adjustable dispersion of the spectrometer may be adjusted based on at least a set spectral width or the adjustable spectral width may be adjusted based on at least a set dispersion of the spectrometer. The provided system allows acquisition of structural data along a depth direction of an object having adjustable axial resolution and adjustable axial field of view. Further, a spectral width of the spectrum of the measuring light illuminating the object may be a minimal spectral width required to achieve a predetermined axial resolution of structural data of the object.

According to an embodiment of the present invention, an amount of spatial separation of the spatially separated spectral portions is adjustable for adjusting the dispersion of the spectrometer. The amount of spatial separation of the spectral portions may for example be determined as a difference of deflection angles by which two different spectral portions are deflected by the spectrometer.

According to an embodiment, the spectrometer comprises a spatially resolving detector for at least partly detecting the spatially separated portions. The detector may be a CCD camera or a CMOS-sensor.

According to an embodiment of the present invention, the controller is adapted to adjust the spectral width and the dispersion of the spectrometer such that a width of an overlap between a wavelength range of the dispersed superimposed light incident onto the positionally resolving detector and the adjusted spectral width amounts to at least 70%, in particular to at least 90% of the adjusted spectral width. Thus, it is possible to illuminate the object with measuring light merely comprising wavelengths that are detected in the superimposed light. Thereby, a total power of measuring light illuminating the object can be reduced to a minimum required to obtain structural information about the object having a given axial resolution. This enables to investigate in particular sensitive biological objects such as a human eye using the inventive system.

According to an embodiment of the present invention, the illumination system comprises at least one spectral filter and a first actuator for arranging the spectral filter into an illumination beam path of the measuring light. Hereby, the spectral width of the spectrum of the measuring light may be affected by the at least one spectral filter. The spectral filter may be a transmission spectral filter or a reflective spectral filter, in particular an interference filter.

According to an embodiment of the present invention, the spectrometer comprises a first diffraction grating and a second actuator for arranging the first diffraction grating into a beam path of the superimposed light. The first diffraction grating may comprise a substrate and plural grating forming structures arranged thereon, in particular in a periodic manner. The grating forming structures may influence an amplitude and/or a phase of the measuring light being incident onto the diffraction grating. The grating forming structures may be periodic that means regularly arranged in at least one lateral dimension of the diffraction grating. In a particular embodiment a diffraction grating comprises straight parallel lines offset from each other by a constant distance. The constant distance corresponds to the lattice period or lattice constant of the first diffraction grating. In a first approximation a diffraction angle of light incident onto the first diffraction grating may be calculated using Bragg's equation. The first and the second actuators may be holding systems such as frames, fixing systems such as a screw, or a spring, switching systems, such as guide ways, which may comprise active driving elements such as motors, or may be free of active driving systems. The actuators may also be driven by manual user intervention.

According to an embodiment of the present invention, the spectrometer comprises an imaging optics arranged in the beam path of the superimposed light upstream of the positionally resolving detector. The imaging optics advantageously allows collecting the superimposed and potentially dispersed light onto the positionally resolving detector, to improve a sensitivity and efficiency of the system. The imaging optics may comprise refractive optical elements such as lenses which may have spherical or aspherical surfaces and may also comprise optical refractive elements having different refractive powers in two different directions perpendicular to an optical axis, such as cylinder lenses.

According to an embodiment of the present invention, the spectrometer comprises a second diffraction grating and the second actuator is further adapted for arranging the second diffraction grating into a beam path of the superimposed light, wherein a lattice constant of the first diffraction grating differs from a lattice constant of the second diffraction grating by at least 10%. Thus, it is possible, in two different operational modes of the system, to disperse the superimposed light into spectral portions which are spatially separated by different amounts. The system may further comprise an optical fibre, in particular a switchable optical fibre to switch a beam path of the superimposed light in order to arrange the first diffraction grating or the second diffraction grating or a combination thereof in a beam path of the superimposed light. For this, the system may further comprise a Micro Electro Mechanical System (MEMS) switch for switching the optical fibre. Fibres and MEMS-switches may be used within the illumination system and the spectrometer of the optical coherence tomography system in order to adjust the spectral width of the spectrum of the measuring light and/or the dispersion of the spectrometer. In particular, the MEMS-switches may be controlled by the controller of the spectral domain optical coherence tomography system.

According to an embodiment of the present invention, a swept-source domain optical coherence tomography (SS-OCT) method is provided which comprises: performing a first measurement and a second measurement, each measurement comprising: illuminating an object region with first measuring light, superimposing first measuring light returned from the illuminated object region with reference light, to from first superimposed light, and detecting an intensity of the first superimposed light, then illuminating the object region with second measuring light, superimposing second measuring light returned from the illuminated object region with reference light, to form second superimposed light, and detecting an intensity of the superimposed light; wherein each of the first and the second measuring lights have a spectral distribution having a peak wavelength and a spectral width, wherein the peak wavelengths differ and wherein an average of the spectral widths during the first measurement is at least two times, in particular five times, greater than an average of the spectral width during the second measurement.

In each of the first measurement and the second measurement, the first measuring light and the second measuring light may correspond to different sweep positions during illuminating the object region in the swept-source OCT method. During both the first measurement and the second measurement further sweep positions may be applied. The spectral widths of the first and the second measuring lights affect an axial depth of view of structural information along a depth direction of the object obtainable by the inventive method. The smaller the spectral widths of the detected superimposed light, the larger is the axial depth of view. Thus, in the present embodiment the axial depth of view is in the first measurement smaller than in the second measurement, in particular at least two times and further in particular at least five times smaller. Concurrently, an axial resolution may be higher during the first measurement than during the second measurement, while the number of spectral samples, e.g. temporal samples, can be kept constant. Thus, it is possible to acquire in the second measurement coarsely resolved structural information about a large volume portion of the object and to acquire in the first measurement more finely resolved structural information about a small volume portion of the object portion. Thus, the inventive method provides zoomable optical coherence tomography.

According to an embodiment of the present invention, the spectral widths are between 200 pm and 5 pm, in particular between 100 pm and 10 pm. Using the measuring light having a spectrum with a mean wavelength of 1 μm and a spectral width of 10 pm for example leads to a theoretical axial depth of view of 5 cm in air. With these parameters the method is capable to structurally investigate for example a human eye having a length of 3.5 cm and an average refractive index of n=1.36. To fully utilize this theoretical axial depth of view, the usage of known techniques to suppress mirror image artifacts could be required, as disclosed in document U.S. Pat. No. 7,330,270 and U.S. Pat. No. 7,336,366 B2.

According to an embodiment of the present invention, the peak wavelengths may be between 800 nm and 1300 nm, in particular between 900 nm and 1100 nm. In particular, the peak wavelength of the first measuring light may differ from the peak wavelength of the second measuring light by at most 10 to 30 nm, in particular at most 25 nm in both the first measurement and the second measurement. This difference in the peak wavelengths may represent a sweeping range of the swept-source OCT method.

According to an embodiment of the present invention, the method further comprises generating measuring light using an optical amplifier, and spectrally filtering the generated measuring light to form first and second measuring lights in at least one of the first and the second measurements. The optical amplifier amplifies electromagnetic waves in a particular working range of wavelengths. Electromagnetic waves having undesired wavelengths may be attenuated to a large degree using the filtering in order to selectively amplify electromagnetic waves having desired wavelengths. Thereby, the spectral width during the first measurement can be changed to the spectral width during the second measurement.

According to an embodiment of the present invention, the filtering comprises allowing the measuring light traversing a transmission spectral filter, in particular a Fabry-Pérot-type filter. A Fabry-Pérot-type filter comprises a pair of opposing reflecting surfaces being arranged parallel to each other having an adjustable distance from each other. Only that part of the measuring light having wavelengths satisfying a resonance condition, i.e. being able to form standing waves between the two reflecting surfaces, will constructively interfere and will eventually emanate from an opening of the filter. The spectral width of the light emanating from the Fabry-Pérot-type filter may be determined from optical properties of the reflecting surfaces of the Fabry-Pérot-type filter.

Further, a mean wavelength of light leaving the Fabry-Pérot-type filter may be controlled by adjusting the distance between the two reflecting surfaces, such as by a piezoelectric element. Thereby, an optical amplifier optically connected to a sweepable Fabry-Pérot-type filter may provide a suitable light source for the swept-source OCT method. Filtering the generated measuring light may be performed during both the first and the second measurements but using different spectral filters having different spectral characteristics, such as two different Fabry-Pérot-type filters having different optical properties of their reflecting surfaces.

According to an embodiment of the present invention, the filtering comprises diffracting the measuring light at a diffraction grating and reflecting the measuring light. The reflecting may comprise reflecting the measuring light at a rotating polygon mirror.

According to an embodiment of the present invention the method further comprises changing a difference between an optical path traversed by at least one of the first measuring light and the second measuring light and an optical path traversed by the reference light.

According to an embodiment of the present invention a maximum of a difference between the peak wavelength of the first measuring light and the peak wavelength of the second measuring light is in the first measurement at least 2 times, in particular 5 times, greater than in the second measurement. Thereby, the resolution of the obtained structural data may be higher in the first measurement than in the second measurement, while concurrently the axial field of view is smaller in the first measurement than in the second measurement. Thus, a zoom effect is achieved.

According to an embodiment of the present invention, a swept-source domain optical coherence tomography (SS- OCT) system is provided which comprises an illumination system for illuminating an object region with measuring light having a spectral distribution having a peak wavelength and a spectral width, wherein the peak wavelength is sweepable and the spectral width is adjustable; a controller for adjusting the spectral width; an interferometer for interferometrically superimposing measuring light returned from the object region with reference light; and a detector for detecting the superimposed light.

The illumination system may comprise a light source and/ or a spectral filter for illuminating the object region with measuring light. The spectral distribution of the measuring light represents a distribution of an intensity of the measuring light in dependence of a wavelength or a related quantity such as a wave number k, being proportional or reciprocal the wavelength. The peak wavelength of the spectrum may be an average or a maximum of the spectral distribution, i.e. the spectrum. The spectral width denotes a width of a main wavelength range comprised in the spectrum. The interferometer may comprise a beam splitter, an optical coupler and an optical fibre. The detector may be a photo-detector that does not need to distinguish intensities of light being incident at different positions of the detector.

According to an embodiment of the present invention, the spectral width is adjustable between 5 pm and 200 pm, in particular between 10 pm and 100 pm.

According to an embodiment of the present invention, the peak wavelength of the measuring light is between 800 nm and 1300 nm, in particular between 600 nm and 1300 nm, in particular between 950 nm and 1050 nm.

According to an embodiment of the present invention, the illumination system comprises an optical amplifier for generating measuring light, a first sweepable spectral filter, and an actuator for arranging the first sweepable spectral filter into a beam path of the generated measuring light.

According to an embodiment of the present invention, the illumination system comprises a second sweepable spectral filter, wherein the actuator is further adapted for arranging the second sweepable spectral filter into the beam path of the generated measuring light. In particular, the second sweepable spectral filter and the first sweepable spectral filter have different filter characteristics. In particular, the two spectral filters may have substantially the same sweeping range but may provide measuring light having different spectral widths.

According to an embodiment of the present invention, at least one of the first and the second spectral filters is a Fabry-Pérot-type filter. The Fabry-Pérot-type filter comprises at least two reflecting surfaces arranged opposed to each other and parallel to each other, to form a resonator in which electromagnetic waves having particular wavelengths may form standing waves. Such a Fabry-Pérot-type filter optically coupled to an optical amplifier may form a light source for the illumination system to generate measuring light having a sweepable peak wavelength and a spectral width specific for an optical characteristics of the reflecting surfaces of the used Fabry-Pérot-type filter. Providing two different Fabry-Pérot-type spectral filters having different optical properties of their reflecting surfaces and being alternatively or in combination arrangeable into an illumination beam path comprising an optical amplifier, thus may form a light source for the illumination system having an adjustable spectral width. In case the first and the second spectral filters are Fabry-Pérot-type filters a range of relative displacements of opposing reflecting surfaces of the two filters may differ by less than 20%, in particular less than 10%.

According to an embodiment of the present invention, at least one of the first and second filters comprises a diffraction grating and a reflector. The reflector may be a rotatable reflector having plural reflecting faces arranged in a peripheral direction around a rotational axis.

According to an embodiment of the present invention, the illumination system is adapted such that the measuring light filtered using the first sweepable spectral filter has a spectral distribution having a first spectral width, the measuring light filtered using the second sweepable spectral filter has a spectral distribution having a second spectral width, wherein the first spectral width is at least two times, in particular at least five times, greater than the second spectral width. The spectral width of the measuring light illuminating the object region, returned from the object region, superimposed with reference light, and detected by the detector affects an axial depth of view of structural information obtained from the object along a depth direction. Thus, the present embodiment enables acquisition of structural data of an object along a first axial depth of view and along a second depth of view, wherein the first depth of view is smaller than the second depth of view. Further, an axial resolution may be selected differently in the two cases by choosing two different sweeping ranges of the measuring light illuminating the object region. Thus, a zoomable OCT system is provided providing enormous advantages in examining biological objects such as a human eye, in particular during surgery.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF THE INVENTION

Figure 1:
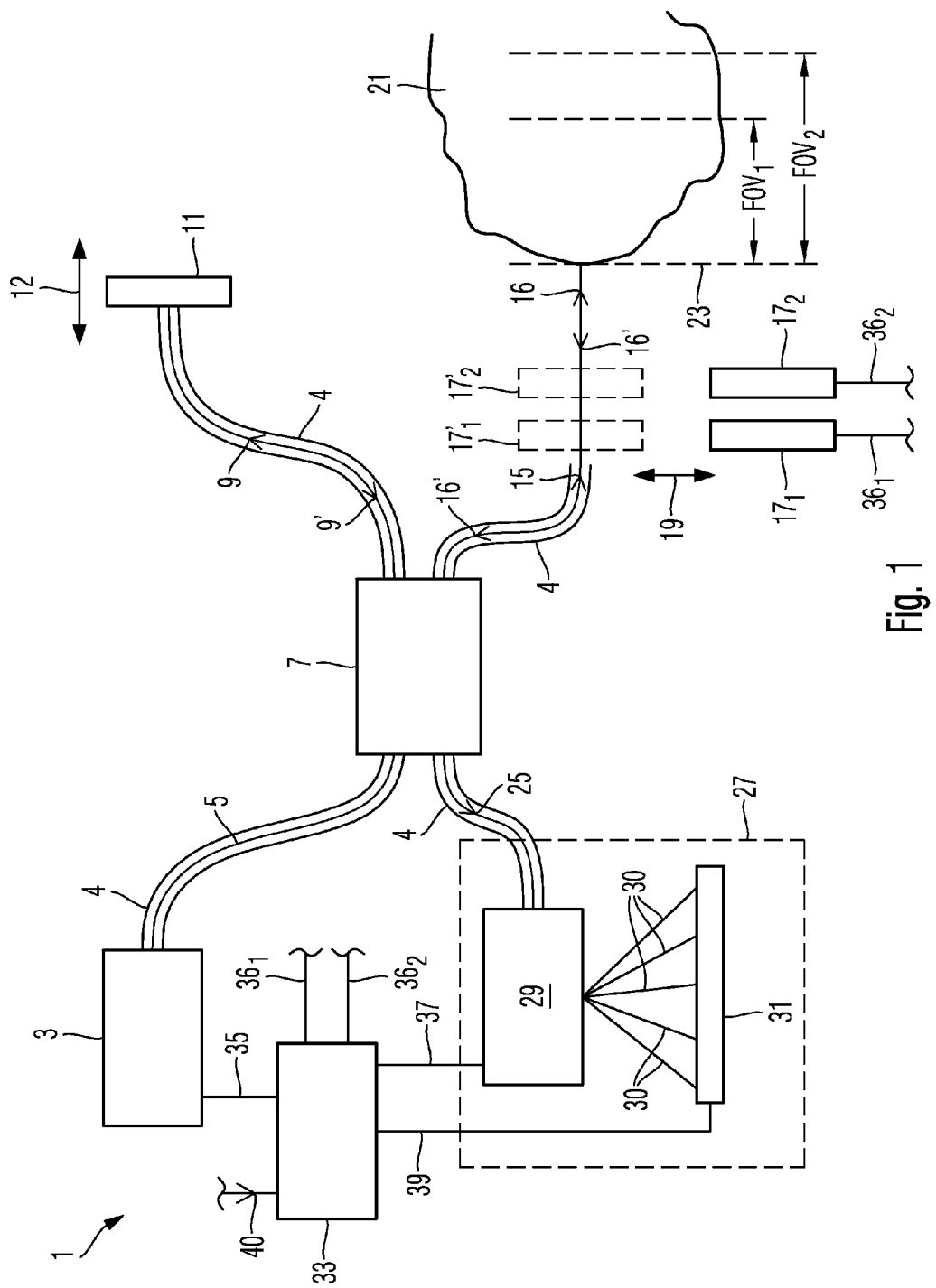
FIG. 1 schematically illustrates a spectral domain OCT system according to an embodiment of the present invention.

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

FIG. 1 schematically illustrates a spectral domain OCT system 1 according to an embodiment of the present invention.

OCT system 1 comprises a light source 3 configured to generate light 5 distributed according to a particular spectrum. There are two variants of this embodiment described below.

In a first variant of the OCT system 1 light source 3 comprises a super-luminescent diode adapted to generate light 5 having a spectrum with a mean wavelength of around 1000 nm and having an adjustable spectral width. The spectral width is adjusted by adjusting an electric current supplied to the super-luminescent diode (SLD). Details of the spectra of light generated by the SLD are described below with reference to FIG. 2.

In a second variant of the OCT system 1 light source 3 comprises a white light source for generating light 5 comprising wavelengths in an extended spectral range. In the second variant the light source 3 may comprise a xenon discharge lamp or a photonic crystal fibre as disclosed by Wang et al., Optics letters, Vol. 28, No. 3, Feb. 1, 2003.

In both variants of the OCT system 1 the generated light 5 is guided by an optical fibre 4 to a fibre splitter/coupler 7. Fibre coupler 7 is configured to split light 5 into two light portions 9 and 15. Light portion 9 is guided via an optical fibre 4 to a reflective reference face 11, where light portion 9 is reflected to form light portion 9'. The reference face 11 is displaceable in directions indicated by double arrow 12, to change a beam path of light portions 9 and 9'. The other light portion 15 separated from light 5 is guided via an optical fibre 4 to a not-illustrated illuminating optics to illuminate an object 21 as light 16. Not illustrated in the schematic FIG. 1 is a scanner, to laterally scan light 16 across the object. Scanning light 16 enables to acquire images comprising structural information. A plane 23 denotes a plane up to which light portion 15 has traveled a beam path having the same optical path length as a beam path traveled by light portion 9 up to the reference face 11.

In the first variant of the OCT system 1, wherein the light source 3 comprises the SLD, light 15 merely traverses the not-illustrated imaging optics to form light 16 illuminating the object 21.

In case of the second variant of the OCT system 1, wherein the light source 3 comprises a xenon gas discharge lamp, light 15 additionally traverses at least one of the spectral filters $17_1$ or/and $17_2$. These spectral filters are arrangeable into a beam path of light 15 as indicated by the arrow 19 and rectangles $17'_1$ and $17'_2$ denoting respective positions of the spectral filters $17_1$, $17_2$, when arranged into the beam path of light 15. The particular location of the filters within the beam path of light illumination the object 21 is not important, as long as they are located somewhere between the light source 3 and the object 21. Thus, FIG. 1 just exemplarily shows one of several potential locations of the spectral filters $17_1$, $17_2$. In order to avoid disturbing back reflexes from the filter(s) arranged in the beam path of light 15, which could lead to artifacts, in a preferred arrangement a normal of the filter(s) $17_1$, $17_2$ deviates from a direction of propagation of the light 15 impinging onto the filter(s) $17_1$, $17_2$.

In both variants the object is finally illuminated by light 16 whose spectral characteristics will be described below with reference to FIG. 2.

Light 16 interacts with the object 21 and emanates from the object as light 16'. Light 16' is guided by the optical fibre 4 to the fibre coupler 7 where it is brought in superposition with light portion 9' formed by reflecting light portion 9 at reference face 11. Superimposed light 25 formed by superimposing light 9' and light 16' leaves the fibre coupler 7, is guided by an optical fibre 4 and enters spectrometer 27. Spectrometer 27 comprises a dispersion device 29 for spectrally dispersing the superimposed light 25 in spatially separated light portions 30. Each light portion 30 comprises electromagnetic light waves having wavelengths within particular different wavelength ranges. The spatially separated light portions 30 are detected by the CCD detector 31 harbouring plural pixels for separately detecting intensities of each of the spatially separated light portions 30.

The spectral domain OCT system 1 further comprises a controller and processing system 33 for controlling several components of the OCT system 1 and for also processing signals generated by the plural pixels of the CCD detector 31 upon detecting the intensities of the plural spatially separated spectral light portions 30. These intensities of detected spectral light portions 30 represent a spectrum of detected superimposed light 25 formed by superposition of reference light 9' and light 16' having interacted with the object 21. The controller and processing system 33 receives the intensities of plural spectral portions 30 detected by the detector 31 via a data transmission line 39, and processes the intensities to derive structural information of the object 21 along a depth direction, i.e. perpendicular to plane 23, of the object 21. The processing comprises background subtraction, spectral resampling, e.g. by sampling at equidistant wave numbers, and determining a Fourier transformation of the spectrum representing the intensities of the plural spectral light portions.

Via a control line 37 the controller and processing system 33 adjusts a dispersion of the dispersion device 29. Adjusting the dispersion of the dispersion device 29 comprises adjusting an amount of spatial separation of the spatially separated light portions 30. The amount of separation of the spatially separated light portions 30 affects a width of a wavelength range of light portions received and detected by a single pixel of the detector 31. This width of a wavelength range of a detected spectral portion of superimposed light 25 in turn affects an effective axial field of view (FOV) of structural information obtainable from the object 21 in the depth direction, i.e. the axial direction which is perpendicular to plane 23. In particular, the controller and processing system 33 is adapted to adjust the dispersion of the dispersion device 29 such that in a first operation mode of system 1 structural information from the object 21 are obtained within a first field of view $FOV_1$ and in a second operation mode of system 1 within a second field of view $FOV_2$, as indicated in FIG. 1.

The controller and processing system 33 adjusts a dispersion of the dispersion device 29 as well as the spectral width of light 16 illuminating the object based on an input signal supplied through signal line 40 as explained below.

In the illustrated embodiment of the spectral domain OCT system 1 the controller and processing system 33 is further adapted to adjust a spectral characteristics of the light 16 illuminating the object 21 differently in the first operation mode and the second operation mode. For this purpose, in particular for the first variant of the OCT system, where the light source 3 comprises a SLD, the controller and processing system 33 adjusts via a control line 35 a spectral width of the spectrum of light 5 generated by the light source. The spectral width of the spectrum of light 5 is adjusted to be different in the first operation mode and the second operation mode. Alternatively or additionally, especially for the second variant of the OCT system 1, wherein the light source 3 comprises a white light source, such as a xenon gas discharge lamp, the controller and processing system 33 controls via control lines $36_1$, $36_2$ not illustrated actuators to arrange spectral filters $17_1$, $17_2$ alternately or in combination into a beam path of light 15. Depending on structural characteristics of the spectral filters $17_1$, $17_2$ the light 16 illuminating the object 21 formed by light 15 having traversed at least one of the spectral filters $17_1$, $17_2$ has a spectrum having a first spectral width or a second spectral width different from the first spectral width. In particular, the controller and processing system 33 is adapted to adjust the spectral width of the light 16 illuminating the object 21 and the dispersion of the dispersion device 29 such that the detected dispersed superimposed light 25 comprises a major portion of wavelengths comprised in the light 16 illuminating the object 21.

Figure 2:
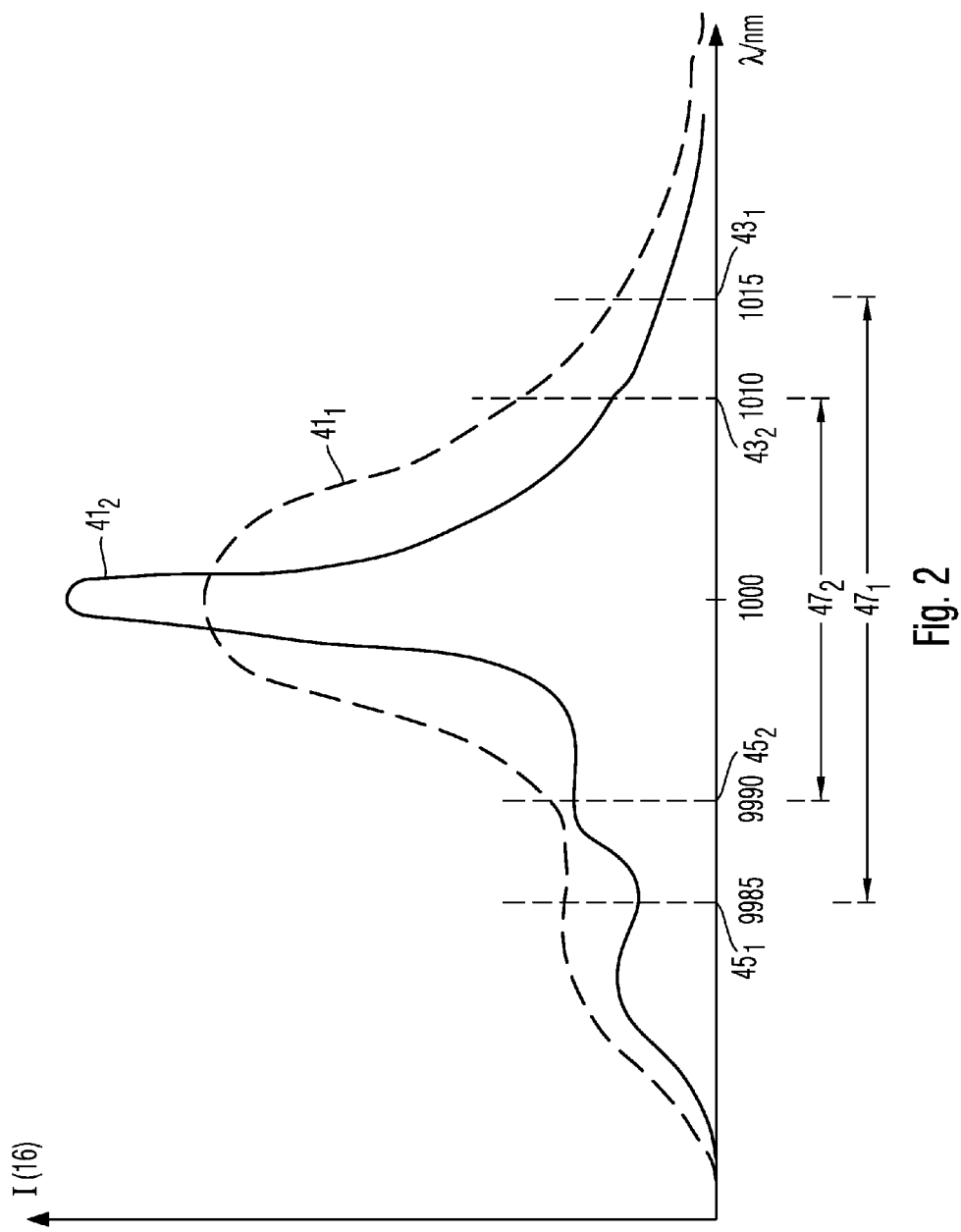
FIG. 2 schematically illustrates a diagram of spectra of measuring light according to embodiments of the present invention.

FIG. 2 illustrates a diagram of a spectrum of light 16 illuminating the object 21. The diagram illustrates curves of relative intensities I(16) in dependence of a wavelength λ. In the first operation mode of the OCT system 1 illustrated in FIG. 1 the object 21 is illuminated with light 16 having a spectrum $41_1$. A mean wavelength of the spectrum $41_1$ lies at around 1000 nm. A spectral width $47_1$ may be obtained by forming a minimum of a difference between a wavelength $43_1$ and a wavelength $45_1$ within which 90% of the integral intensity of light 16 is comprised. In the illustrated example the first spectral width being the spectral width of light 16 illuminating the object in the first operation mode amounts to about 30 nm.

In the second mode of operation, the object 21 is illuminated with light 16 having a spectrum $41_2$. The mean wavelength of spectrum $41_2$ amounts to about the same as the mean wavelength of spectrum $41_1$, namely around 1000 nm. However, the second spectral width, i.e. the spectral width of the spectrum of light 16 illuminating the object 21 during the second operation mode, is smaller than the first spectral width, namely 20 nm in the illustrated example. The second spectral width is again obtained by determining a minimum of a difference between a wavelength $43_2$ and a wavelength $45_2$ within which 90% of the integral intensity of light 16 is comprised.

In the first variant of the spectral domain OCT system 1 illustrated in FIG. 1 the curves $41_1$, $41_2$ may resemble emission spectra of a super-luminescent diode operated at two different electric currents. In this case, there may be no additional spectral filter, such as spectral filters $17_1$, $17_2$, required to adjust a spectrum and thus a spectral width of the spectrum of the light 16 illuminating the object 21.

For the second variant of the spectral source OCT system 1 illustrated in FIG. 1, the curves $41_1$, $41_2$ illustrated in FIG. 2 may resemble transmission characteristics of spectral filters $17_1$, $17_2$, respectively.

Figure 3:
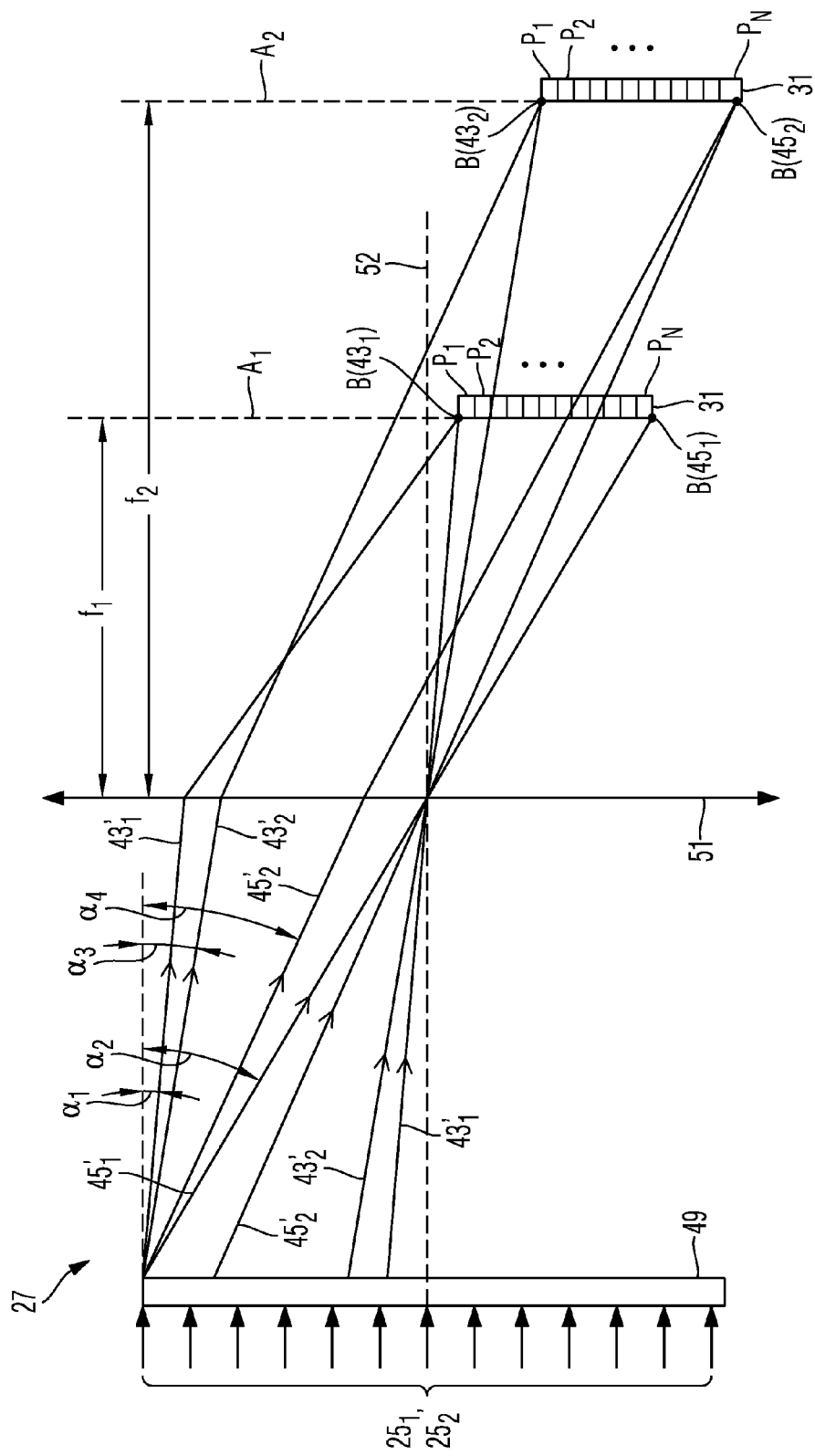
FIG. 3 schematically illustrates a portion of a spectrometer used in embodiments of the present invention, such as the embodiment illustrated in FIG. 1.

FIG. 3 schematically illustrates a spectrometer 27 that may be used in the embodiment of a spectral domain OCT system illustrated in FIG. 1. The spectrometer comprises a diffraction grating 49, imaging optics 51 having an adjustable focal length, and detector 31 which is here illustrated at two different positions $A_1$ and $A_2$ in the first and second operation modes, respectively. The imaging optics 51 has an optical axis 52. The diffraction grating 49 comprises plural grating forming structures arranged thereon in a periodic manner. In the illustrated example the grating forming structures comprise regularly spaced straight protrusions. The spacing between neighbouring protrusions is in the range of wavelengths of the superimposed light 25 being incident onto the grating 49.

During the first operation mode superimposed light $25_1$ forming substantially parallel wavefronts is incident onto the grating 49 and in the second operation mode superimposed light $25_2$ is incident onto the diffraction grating 49. Superimposed light $25_1$ is deflected by diffraction at the grating 49 at different deflection angles depending on its wavelengths. As illustrated in FIG. 2 the light 16 illuminating the object 21 in the first operation mode mainly comprises wavelengths between wavelengths $45_1$ and $43_1$. Thus, also the superimposed light $25_1$ mainly comprises wavelengths between wavelength $45_1$ and wavelength $43_1$. In FIG. 3 a beam path of light $25_1$ having a wavelength $43_1$ is denoted as $43'_1$. A beam path of light $25_1$, having a wavelength $45_1$ is denoted as $45'_1$. Light $25_1$ having a wavelength $43_1$ is deflected by diffraction at the grating 49 at an angle α1, and light $25_1$ having a wavelength $45_1$ is deflected by diffraction at the grating 49 at an angle $α_2$, wherein the angles are measured with respect to a normal of grating 49 which is oriented parallel to optical axis 52. Light $25_1$ having wavelengths between wavelength $43_1$ and wavelength $45_1$ comprised in the superimposed light $25_1$ is deflected by diffraction at the grating 49 at angles in between the extreme angles $α_1$ and $α_2$. Diffracted light rays propagating along the beam paths $43'_1$ and $45'_1$ traverse the imaging optics 51 adjusted to have a focal length $f_1$. The focal plane of the imaging optics 51 having the focal length $f_1$ is indicated in FIG. 3 and labeled as $A_1$.

In the first operation mode the CCD detector 31 is arranged in the focal plane A1 of the imaging optics 51 downstream the imaging optics 51. The CCD detector comprises pixels $P_1$, $P_2$, ..., $P_N$. By the imaging optics 51 a light ray traversing the beam path $43'_1$ is imaged at a point $B(43_1)$. Light ray propagating along beam path $45'_1$ is imaged at a point $B(45_1)$. The points $B(43_1)$ and $B(45_1)$ are located at border pixels of the detector, namely $P_1$ and $P_N$, respectively. Light comprised in superimposed light $25_1$ having wavelength between the wavelengths $43_1$ and $45_1$ is deflected by diffraction at grating 49 at an angle between the angles $α_1$ and $α_2$ and thus imaged to pixels of the CCD detector 31 between the border pixels $P_1$ and $P_N$. Thus, during the first operation mode light having wavelengths between wavelengths $43_1$ and $45_1$, amounting to 90% of the intensity of superimposed light $45_1$, is spectrally resolved detected by detector 31. Each pixel receives light having wavelengths within a wavelength range having a width of $(43_1-45_1)/N$.

During the second operation mode superimposed light $25_2$ is incident on the diffraction grating 49. In the second operation mode light 16 illuminating the object has a spectrum having the second spectral width $47_2$, obtained by the difference of wavelengths $43_2$ and $45_2$. Light having a wavelength $43_2$ comprised in superimposed light $25_2$ is deflected by diffraction at the diffraction grating at an angle $α_3$ and light having a wavelength $45_2$ comprised in superimposed light $25_2$ is deflected by diffraction at grating 49 at an angle α4. Corresponding beam paths for light having a wavelength $43_2$ are denoted as $43'_2$ and the beams path of light having a wavelength $45_2$ are denoted as $45'_2$. Light comprised in superimposed light $25_2$ having wavelengths between the wavelengths $45_2$ and $43_2$ is deflected at an angle between angles $α_3$ and $α_4$.

During the second operation mode the focal length of the imaging optics 51 has been changed to be $f_2$. Further, the detector, namely its light sensitive surface, has been displaced to be arranged within the focal plane $A_2$ of the imaging optics 51 being adjusted to have now the focal length $f_2$. By traversing the imaging optics 51 light propagating along $43'_2$ is imaged at a point $B(43_2)$. Light comprised in superimposed light $25_2$ propagating along $45'_2$ is imaged by the imaging optics at point $B(45_2)$. These points $B(43_2)$ and $B(45_2)$ are located at border pixels $P_1$ and $P_N$ of the detector 31, respectively. Light comprised in superimposed light 252 having a wavelength between wavelengths $43_2$ and $45_2$ will be imaged at a pixel in between border pixel $P_1$ and $P_N$. Thus, also in the second operation mode detector 31 receives light having wavelengths comprising 90% of an intensity of superimposed light $25_2$ and thus 90% of an intensity of light 16 illuminating the object 21. In this operation mode a width of a wavelength range received by every of the N pixels of the detector 31 is $(43_2-45_2)/N$, i.e. (second spectral width)/N. Since the first spectral width is larger than the second spectral width the width of a wavelength range received by a single pixel is larger in the first operation mode than in the second operation mode. Thus, the axial field of view (FOV) $FOV_1$ in the first operation mode is smaller than the axial field of view $FOV_2$ in the second operation mode, as also indicated in FIG. 1.

In the spectrometer 27 illustrated in FIG. 3 an imaging of superimposed lights $25_1$, $25_2$ having a spectrum with different spectral widths to an area of substantially the same size, i.e. to the area of the detector 31, has been achieved by varying the focal length of the imaging optics 51 from focal length $f_1$ to focal length $f_2$ and displacing the detector 31 to be arranged in the respective focal plane $A_1$ and $A_2$, respectively. Alternatively or additionally two different gratings 49 having different lattice constants, prisms, or combinations thereof, may be utilized during the first operation mode or/and the second operation mode for diffracting and thus deflecting the superimposed lights $25_1$, $25_2$. All such provisions will change an amount of separation of plural spectral light portions for adjusting the dispersion of the spectrometer 27.

Figure 4:
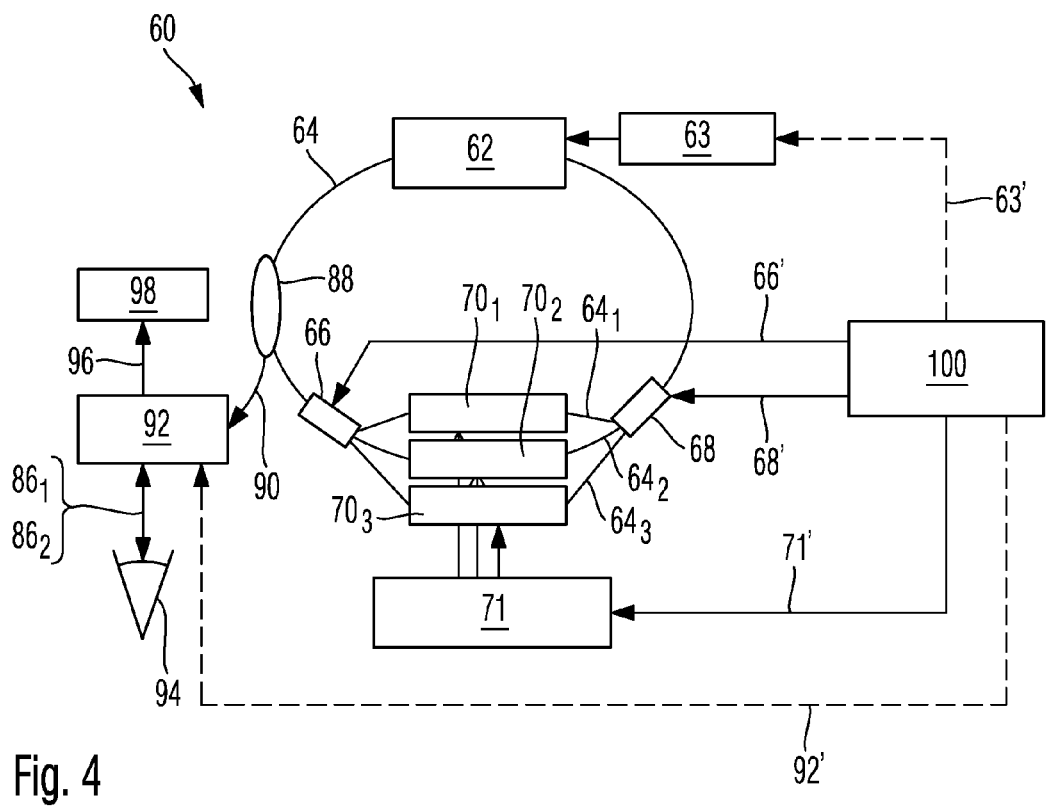
FIG. 4 schematically illustrates a swept-source OCT system according to an embodiment of the present invention.

FIG. 4 schematically illustrates a swept-source domain OCT system 60 according to an embodiment of the present invention. Swept-source domain OCT system 60 comprises a semiconductor optical amplifier 62 for amplifying light waves in a working wavelength range. For this, semiconductor optical amplifier 62 is pumped by a current source 63. Semiconductor optical amplifier 62 is optically connected to a ring fibre 64 for guiding light amplified by the optical amplifier 62. In a beam path guided by the optical fibre 64 routing switches 66 and 68 are arranged that are adapted to guide light propagating within the optical fibre 64 to optical fibers $64_1$, $64_2$, or $64_3$. Optical fibre $64_1$ guides light introduced from either the routing switch 66 or 68 into a first sweepable filter $70_1$ allowing the light traversing the first sweepable filter $70_1$. After traversing the first sweepable filter light is reintroduced via routing switch 66 or 68 into the fibre ring 64. Alternatively to traversing the first sweepable filter $70_1$ a second sweepable filter $70_2$ or a third sweepable filter $70_3$ may be traversed by the light guided by optical fibre 64 by guiding the light to fibre $64_2$ and $64_3$, respectively.

The first, second and third sweepable filters $70_1$, $70_2$, $70_3$ are Fabry-Pérot-type spectral filters comprising two opposing reflecting surfaces arranged parallel to each other. A distance between the two reflective surfaces is controllable via a piezoelectric element driving by a ramp generator 71 that is connected to all three filters. Only light having a wavelength satisfying a resonance condition depending on a distance between the two opposing reflecting surfaces of the Fabry-Pérot-type spectral filter arranged in beam path of ring resonator will constructively interfere. By changing the distance between the two opposing reflecting surfaces of the Fabry-Pérot-type filter using the ramp generator 71 a wavelength of light satisfying the resonance condition can be varied. Light having a wavelength different from a wavelength satisfying the resonance condition will destructively interfere and thus will be decreased to very low intensities. Depending on the optical property of the opposing reflecting surfaces of a Fabry-Pérot-type filter not only one single wavelength satisfies the resonance condition but a range of wavelengths around a peak wavelength, forming a transmission spectrum whose characteristics depends on at least a reflectivity of the reflective surfaces.

Figure 5:
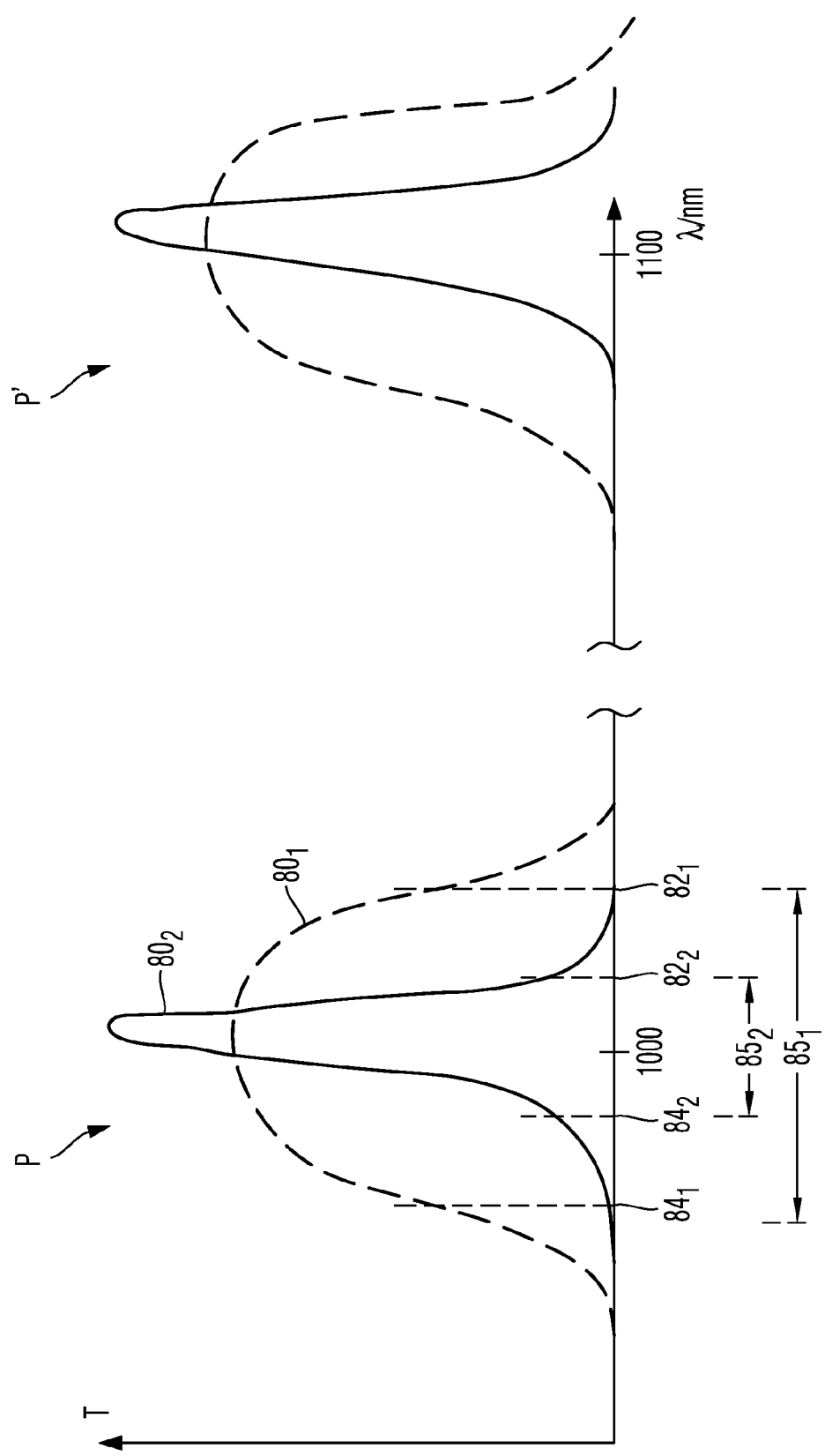
FIG. 5 illustrates a diagram showing filter characteristics of spectral filters used in embodiments of swept-source OCT systems according to the present invention, such as embodiments illustrated in FIGS. 4 and 6.

FIG. 5 illustrates a diagram showing a transmission characteristics T of the first and second sweepable filters $70_1$, $70_2$ illustrated in FIG. 4. Dependent on the wavelength λ a transmission of the first sweepable filter $70_1$ denoted as curve $80_1$ and a transmission of the second sweepable filter $70_2$, denoted as $80_2$, is depicted. Typically each Fabry-Pérot-type filter exhibits plural transmission peaks. In the diagram two such transmission peaks P, P' are shown, one having a mean wavelength of 1000 nm and another having a mean wavelength of 1100 nm. Plural transmission peaks occur, because the resonance condition may be satisfied by plural wavelengths according to different orders. Here, only the first transmission peak P located around 1000 nm is of interest, since the second transmission peak P' located around 1100 nm lies outside the wavelength working range of the semiconductor optical amplifier 62 and is therefore not amplified.

A first spectral width $85_1$ of the transmission spectrum $80_1$ of the first sweepable filter $70_1$ may be obtained by forming a minimum of a difference between two wavelengths $82_1$ and $84_1$ within which 90% of the transmission $80_1$ of the first sweepable filter $70_1$ lies disregarding transmission peaks of higher order wavelengths outside the working range of the semiconductor optical amplifier. In the illustrated example, the first spectral width $85_1$ amounts to about 50 pm. Analogously a second spectral width $85_2$ of the transmission spectrum $80_2$ of the second sweepable filter $70_2$ may be obtained which amounts to about 20 pm.

Referring again to FIG. 4, when the first sweepable filter $70_1$ is arranged to be optically coupled to the optical ring fibre 64 and thus to the optical amplifier 62, only light will be amplified by the semiconductor optical amplifier 62 that substantially has a spectrum given by the transmission spectrum $80_1$ of the first sweepable filter $70_1$. The thus amplified light will be denoted as light $86_1$. Light $86_1$ guided within the ring fibre 64 is partly extracted from the ring fibre 64 by optical coupler/splitter 88 and is guided via optical fibre 90 to interferometer 92. Light $86_1$ illuminates an object 94, returns from the object and is superimposed with not illustrated reference light within the interferometer 92. Illuminating the object 94 may comprise scanning light $86_1$ across the object using a not illustrated scanner comprising at least one reflecting surface rotatable in one direction. Superimposed light is guided via optical fibre 96 to a photodetector 98. At a particular point in time detector 98 merely detects light having interacted with the object 94 and being superimposed with reference light which has a spectrum substantially given by the transmission spectrum of the first sweepable filter 701, as denoted by curve $80_1$ in FIG. 5.

To acquire a spectrum of superimposed light across a broader spectral range, the piezoelectric element comprised in the first sweepable filter $70_1$ is actuated to change the distance between the two opposing reflecting faces of the first sweepable filter $70_1$. For this purpose the ramp generator 71 controlled by a controller 100 supplies a ramp signal to filter $70_1$ to change the distance between the two opposing reflecting faces of the Fabry-Pérot-type filter $70_1$. Thereby a mean wavelength of the transmission spectrum $70_1$ of the first sweepable filter $70_1$ changes, since the resonance condition is satisfied for slightly different wavelengths compared to the previous distance between the two opposing reflecting surfaces of the first sweepable filter $70_1$. Thus, sweeping of an amplified mean wavelength may be performed. However, due to the constant optical properties of the reflecting faces of the first sweepable filter $70_1$ the first spectral width $85_1$ substantially stays constant during sweeping the mean wavelength of the transmission spectrum.

As explained above in relation to the spectral domain OCT systems and methods, a spectral width received by a detector or a detector segment effects an axial field of view of structural information obtainable from the object 94 along a depth direction. In order to switch an axial field of view the present invention enables arranging the second sweepable filter $70_2$ into a beam path of light being amplified by the semiconductor optical amplifier 62 by actuating the routing switches 66 and 68 controlled by the controller 100 via signal lines 66' and 68', respectively, in order to optically connect the fibers $64_2$ to the optical fibre 64. Thereby, in a second operation mode the object 94 is illuminated with light $86_2$ comprising wavelengths distributed according to substantially the transmission spectrum $80_2$ of the second sweepable filter $70_2$ having the second spectral width $85_2$. Accordingly, superimposed light having wavelengths distributed according to the curve $80_2$ is detected by the detector 98. Since the first spectral width during the first operation mode is greater than the second spectral width in the second operation mode an axial field of view is smaller in the first operation mode than in the second operation mode.

The controller 100 is provided to control the swept-source OCT system 60 in the two operation modes. For this the controller drives the switches 66 and 68 via signal lines 66' and 68' for arranging the first $70_1$ or the second $70_2$ sweepable filters into a beam path of light finally illuminating the object 94. Further, the controller 100 is adapted to control sweeping the mean wavelengths of the transmission spectra of the sweepable filters by controlling the piezoelectric elements via the ramp generator 71 using signal line 71'. Further the controller 100 may adjust attenuation of the reference arm or/and an optical path traveled by the reference light within interferometer 92 via signal line 92'. Also controller 100 controls the current source 63 pumping the optical amplifier 62.

Figure 6:
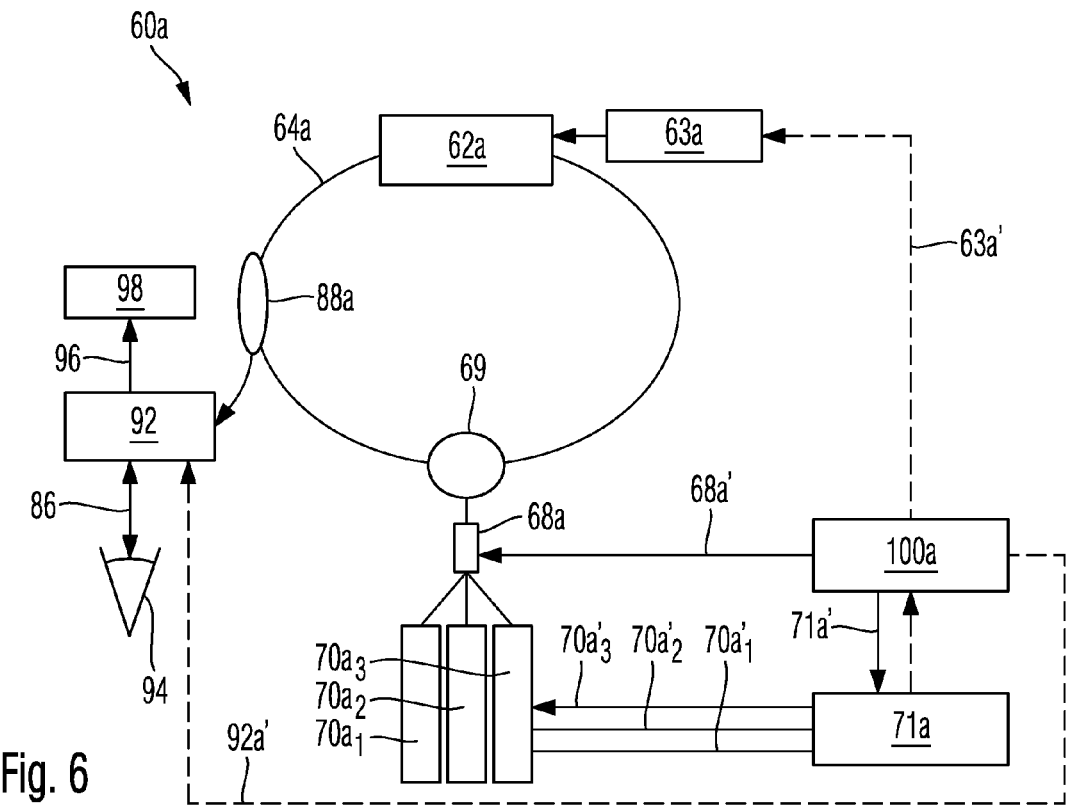
FIG. 6 schematically illustrates another embodiment of a swept-source OCT system according to the present invention.

FIG. 6 illustrates another embodiment of a swept-source OCT system 60a according to the present invention. A number of elements and components comprised in the swept-source OCT system 60a are similar to those comprised in swept-source OCT system 60 illustrated in FIG. 4. A difference between these two swept-source OCT systems is that in system 60 transmission spectral filters $70_1$, $70_2$, $70_3$ are employed, whereas in system 60a reflective spectral filters $70a_1$, $70a_2$, $70a_3$ are employed. In particular, sweepable spectral reflective filters are used which may comprise a diffraction grating and a beam deflecting device such as a polygon mirror scanner. In particular, the polygon mirror scanner may be rotatable to sweep a transmission spectrum of the sweepable reflective filter. The different sweepable reflective filters $70a_1$, $70a_2$, $70a_3$ provide different transmission spectra, in particular regarding spectral widths of their transmission spectra. The sweepable reflective filters may be alternatively or in combination arranged in a beam path of light travelling along ring fibre 64a illuminating the sample 94 by controlling a routing switch 68a by the controller 100a via signal line 68a'. Light travelling along ring fibre 64a is guided via circulator 69 to one of filters $70a_1$, $70a_2$, $70a_3$ depending on a setting of routing switch 68a. In this embodiment, only one routing switch is required. As in the system 60 illustrated in FIG. 4 the controller 100a is adapted to control sweeping the mean wavelengths of the transmission spectra of the sweepable reflective filters via signal lines $70a'_1$, $70a'_2$, $70a'_3$, connected to ramp generator 71a which in turn is controlled via signal line 71a' by controller 100a. Via signal line 71a' the ramp generator 71a supplies a signal to the controller 100a that may be used by controller 100a to switch filters between forward and backward ramps. Via signal line 63' and 63a' in FIG. 4 and FIG. 6 the controller controls the current source 63 and 63a, respectively, pumping the optical amplifier.

The frequency domain OCT systems according to the present invention may further comprise a scanner for laterally scanning a measuring light beam across a region of the object to be investigated. The scanner may comprise at least one mirror pivotable in at least one direction.

The swept-source OCT system may further comprise a reference interferometer which is adapted to analyze measuring light illuminating the object at a given time point with respect to the mean wavelength (k-clock). Thereby, the swept-source OCT system can be calibrated in order to obtain a relationship between sweeping time and mean wavelength of the illuminating measuring light.

Embodiments according to the present invention can advantageously be applied to ophthalmologic applications. In some applications it may be desired to attenuate an intensity of the reference light, in particular in dependence of an adjusted spectral width of measuring light illuminating the object. Further, the controller and processing system in embodiments of the present invention may be adapted to selectively read out pixels of the detector, in particular in dependence of an adjusted spectral width of measuring light illuminating the object, or in dependence of an adjusted dispersion of the spectrometer. Further, an exposure time and/or gain of the detector may be adjusted depending on the adjusted spectral width of the measuring light illuminating the object.

Embodiments according to the present invention can advantageously be employed to reduce radiation damage of biological objects during examination. Further, different axial fields of view can quickly be switched to acquire recordings of structural information of the object across different axial fields of view. For switching for example Micro Electro Mechanical Systems may be employed which enables switching in a time scale of 1 to 50 ms.

Summarized, frequency domain optical coherence tomography (FD-OCT) systems and methods are provided. Thereby, a first measurement and a second measurement is performed, wherein in the first measurement an object region is illuminated by measuring light having a spectrum with a first spectral width and in the second measurement the object region is illuminated with measuring light having a spectrum with a second spectral width, wherein the first spectral width is at least 10% greater than the second spectral width. Further, during the first measurement intensities of spectral portions of light having interacted with the object and being superimposed with reference light are detected, wherein a width of these spectral portions is greater than a corresponding width during the second measurement. Thus, switching an axial field of view of structural information of the object along a depth direction is enabled upon minimizing radiation damage at the object.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. A spectral domain optical coherence tomography (SD-OCT) method comprising: performing a first measurement and a second measurement, each measurement comprising:
   illuminating an object region with measuring light;
   superimposing measuring light returned from the object region with reference light;
   spectrally dispersing the superimposed light; and
   detecting intensities of plural different spectral portions of the spectrally dispersed light;
   wherein during the first measurement, the measuring light illuminating the object region is spectrally distributed according to a first spectrum; and during the second measurement, the measuring light illuminating the object region is spectrally distributed according to a second spectrum, and wherein a first spectral width of the first spectrum is at least 10% greater than a second spectral width of the second spectrum;

wherein the first spectral width is determined to be a minimum of a difference between a first upper wavelength and a first lower wavelength;

wherein during the first measurement, an intensity of the measuring light having wavelengths between the first lower wavelength and the first upper wavelength amounts to 90% of a total intensity of the measuring light;

wherein the second spectral width is determined to be a minimum of a difference between a second upper wavelength and a second lower wavelength;

wherein during the second measurement, an intensity of the measuring light having wavelengths between the second lower wavelength and the second upper wavelength amounts to 90% of a total intensity of the measuring light; and wherein a width of a wavelength range comprised in each of the spectral portions during the first measurement is greater than a width of a wavelength range comprised in each of the spectral portions during the second measurement.

2. The method according to claim 1 wherein in the first measurement, the plural different spectral portions are within a predetermined first detection wavelength range; and in the second measurement, the plural different spectral portions are within a predetermined second detection wavelength range;

wherein a width of the first detection wavelength range is greater than a width of the second detection wavelength range.

3. The method according to claim 2 wherein at least one of the following in satisfied:

a ratio between the width of the first detection wavelength range and the first spectral width amounts to at least 0.9 or amounts to 1.0; or a ratio between the width of the second detection wavelength range and the second spectral width amounts to at least 0.9 or amounts to 1.0.

4. The method of claim 3, wherein each of the first and the second spectrum is a continuous spectrum.

5. The method according to claim 1 wherein detecting the intensities of the plural different spectral portions comprises detecting the intensities at plural different positions of a positionally resolving detector.

6. The method according to claim 1 wherein in at least one of the first measurement or the second measurement, dispersing the superimposed light comprises diffracting the superimposed light at a first diffraction grating.

7. The method according to claim 6 wherein dispersing the superimposed light comprises allowing the diffracted light to traverse an imaging optics.

8. The method according to claim 7 wherein during both the first and second measurements, dispersing the superimposed light comprises diffracting the superimposed light at the first diffraction grating; and wherein during the first measurement, the imaging optics has a first focal length and during the second measurement, the imaging optics has a second focal length at least 10% greater than the first focal length.

9. The method according to claim 6 wherein during the second measurement, dispersing the superimposed light comprises diffracting the superimposed light at a second diffraction grating;

wherein a lattice period of the first diffraction grating is at least 10 greater than a lattice period of the second diffraction grating.

10. The method according to claim 1 wherein illuminating the object region comprises scanning an illumination beam of measuring light across the object region, the illumination beam having a beam waist located at an average depth of the object region such that a Rayleigh range of the illumination beam substantially corresponds to an axial field of view of the OCT-method.

11. The method according to claim 1 further comprising changing a difference between an optical path traversed by the measuring light and an optical path traversed by the reference light.

12. The method of claim 1, wherein the width of the wavelength range during the first measurement and the second measurement is such that an axial field of view of the measuring light in the second measurement is at least 10% greater than in the first measurement.

13. The method of claim 1, wherein the width of the wavelength range during the first measurement and the second measurement is such that an axial field of view of the measuring light in the second measurement is at least 20% greater or at least 50% greater than in the first measurement.

14. The method of claim 1, wherein each of the first and the second spectrum is a continuous spectrum.

15. A spectral domain optical coherence tomography (SD-OCT) system, the system comprising: an illumination system having a light source for illuminating an object region with measuring light, wherein a spectral width of a spectrum of the measuring light is adjustable;

a spectrometer having an adjustable dispersion for spectrally dispersing measuring light returned from the object region and superimposed with reference light into plural spatially separated different spectral portions; and a controller which is configured to switch between a first and a second operation mode of the system by adjusting the adjustable spectral width and adjusting the adjustable dispersion of the spectrometer based on an input signal;

wherein in the first operation mode, the measuring light illuminating the object region is spectrally distributed according to a first spectrum having a first spectral width; and in the second operation mode, the measuring light illuminating the object region is spectrally distributed according to a second spectrum having a second spectral width;

wherein the first spectral width is at least 10% greater than the second spectral width;

wherein the first spectral width is determined to be a minimum of a difference between a first upper wavelength and a first lower wavelength;

wherein in the first operation mode, an intensity of the measuring light having wavelengths between the first lower wavelength and the first upper wavelength amounts to 90% of a total intensity of the measuring light;

wherein the second spectral width is determined to be a minimum of a difference between a second upper wavelength and a second lower wavelength;

wherein in the second operation mode, an intensity of the measuring light having wavelengths between the second lower wavelength and the second upper wavelength amounts to 90% of a total intensity of the measuring light; and wherein a width of a wavelength range comprised in each of the spectral portions in the first operation mode is greater than a width of a wavelength range comprised in each of the spectral portions in the second operation mode.

16. The system according to claim 15 wherein an amount of spatial separation of the plural spatially separated spectral portions is adjustable for adjusting the dispersion of the spectrometer.

17. The system according to claim 15 wherein
the spectrometer comprises a spatially resolving detector for at least partly detecting the plural spatially separated spectral portions.

18. The system according to claim 17 wherein the spectrometer comprises an imaging optics arranged in the beam path of the superimposed light upstream of the positionally resolving detector.

19. The system according to claim 15 wherein the controller is adapted to adjust the spectral width and the dispersion of the spectrometer such that a width of an overlap between a wavelength range of an adjusted dispersed superimposed light incident on the positionally resolving detector and the adjusted spectral width amounts to at least 90% of the adjusted spectral width or amounts to 100% of the adjusted width.

20. The system of claim 19, wherein each of the first and the second spectrum is a continuous spectrum.

21. The system according to claim 15 wherein at least one of the following holds:
the illumination system comprises at least one spectral filter and a first actuator configured to arrange the spectral filter in an illumination beam path between the light source and the object to adjust the spectral width; and
the light source comprises a super-luminescent diode, wherein the controller is configured to adjust the spectral width by adjusting an electric current supplied to the super-luminescent diode.

22. The system according to claim 15 wherein the spectrometer comprises a first diffraction grating and a second actuator for arranging the first diffraction grating in a beam path of the superimposed light.

23. The system of claim 15, wherein the width of the wavelength range during the first and the second operation mode is such that an axial field of view of the measuring light in the second operation mode is at least 10% greater than in the first operation mode.

24. The system of claim 15, wherein the width of the wavelength range during the first and the second operation mode is such that an axial field of view of the measuring light in the second operation mode is at least 20% greater or at least 50% greater than in the first operation mode.

25. The system of claim 15, wherein each of the first and the second spectrum is a continuous spectrum.

26. A Swept source domain optical coherence tomography (SSOCT) method comprising: performing a first measurement and a second measurement, each measurement comprising:
illuminating an object region with first measuring light;
superimposing first measuring light returned from the illuminated object region with reference light, to form first superimposed light; and
detecting an intensity of the first superimposed light; then
illuminating the object region with second measuring light;
superimposing second measuring light returned from the illuminated object region with reference light, to form second superimposed light; and
detecting an intensity of the second superimposed light;
wherein each of the first and the second measuring lights has a spectral distribution having a peak wavelength and a spectral width,
wherein the spectral width of each of the spectral distributions is determined by a minimum of a difference between two wavelengths, between which 90% of an intensity of the respective spectral distribution is located;
wherein in each of the first and the second measurement, a difference between the peak wavelength of the first measuring light and the peak wavelength of the second measuring light represents a sweeping range of the respective measurement;
wherein the sweeping range of the first measurement is at least 2 times greater or 5 times greater than in the second measurement; and
wherein an average of the spectral widths during the first measurement is at least 2 times greater than an average of the spectral widths during the second measurement.

27. The method according to claim 26 wherein the average of the spectral widths during the first measurement is at least 5 times greater than the average of the spectral widths during the second measurement.

28. The method according to claim 26 wherein the peak wavelengths are between 800 nm and 1300 nm.

29. The method according to claim 28 wherein the peak wavelengths are between 900 nm and 1100 nm.

30. The method according to claim 26 further comprising: generating measuring light using a semiconductor optical amplifier; and spectrally filtering the generated measuring light to form first and second measuring lights in at least one of the first measurement or the second measurement.

31. The method according to claim 30 wherein spectrally filtering comprises diffracting the measuring light at a diffraction grating and reflecting the measuring light.

32. The method according to claim 26 further comprising changing a difference between an optical path traversed by at least one of the first measuring light or the second measuring light and an optical path traversed by the reference light.

33. A Swept source domain optical coherence tomography (SSOCT) system, the system comprising:
an illumination system for illuminating an object region with measuring light having a spectral distribution having a peak wavelength and a spectral width, wherein the peak wavelength is sweepable and the spectral width is adjustable;
wherein the spectral width of the spectral distribution is determined by a minimum of a difference between two wavelengths, between which 90% of an intensity of the spectral distribution is located;
an interferometer for interferometrically superimposing measuring light returned from the object region with reference light; and
a detector for detecting the superimposed light;
a controller which is configured to switch between a first and a second operation mode of the system by adjusting the spectral width and controlling a sweeping of the peak wavelength over a sweeping range;
wherein an average of the spectral width in the first operation mode is at least 2 times greater than an average of the spectral width in the second operation mode; and wherein the sweeping range of the first measurement is at least 2 times greater, or is 5 times greater than in the second measurement.

34. The system according to claim 33 wherein the spectral width is adjustable between 5 pm and 200 pm.

35. The system according to claim 34 wherein the spectral width is adjustable between 10 pm and 100 pm.

36. The system according to claim 33 wherein the peak wavelength of the measuring light is between 800 nm and 1300 nm or between 950 nm and 1050 nm.

37. The system according to claim 33 wherein the illumination system comprises:
- a semiconductor optical amplifier for generating measuring light; and
- a first sweepable spectral filter; and an actuator for arranging the first sweepable spectral filter in a beam path of the generated measuring light.

38. The system according to claim 37 wherein the illumination system comprises a second sweepable spectral filter, wherein the actuator is further adapted for arranging the second sweepable spectral filter in the beam path of the generated measuring light, wherein filter characteristics of the first and second sweepable spectral filters are different.

39. The system according to claim 38 wherein the illumination system is adapted such that:

the measuring light filtered using the first sweepable spectral filter has a spectral distribution having a first spectral width;

and the measuring light filtered using the second sweepable spectral filter has a spectral distribution having a second spectral width;

wherein the first spectral width is at least 2 times greater than the second spectral width.

40. The system according to claim 39 wherein the first spectral width is at least 5 times greater than the second spectral width.

41. The system according to claim 37 wherein at least one of the first spectral filter or the second spectral filter comprises a Fabry-Pérot-type filter.

42. The system according to claim 37 wherein at least one of the first spectral filter or the second filter comprises a diffraction grating and a reflector.

43. The method of claim 1, further comprising at least one of the following:
- arranging a spectral filter in an illumination beam path between the light source and the object to adjust between the first spectral width and the second spectral width; and
- adjusting an electric current supplied to a super-luminescent diode, which generates the measuring light, to adjust between the first spectral width and the second spectral width.

* * * * *

UNITED STATES PATENT AND TRADEMARK OFFICE
CERTIFICATE OF CORRECTION

PATENT NO. : 8,427,653 B2  
APPLICATION NO. : 13/007470  
DATED : April 23, 2013  
INVENTOR(S) : Hacker et al.

Page 1 of 1

It is certified that error appears in the above-identified patent and that said Letters Patent is hereby corrected as shown below:

In the Claims

Column 22, Claim 9, line 6, "10" should read --10%--.

Signed and Sealed this
Twenty-fifth Day of March, 2014

Michelle K. Lee
*Deputy Director of the United States Patent and Trademark Office*